United States Patent
van der Burg

[11] 4,054,572
[45] Oct. 18, 1977

[54] HEXAHYDRO PYRIDINE [1,2D] DIBENZA [B,F] (1,4)-DIAZEPINES

[75] Inventor: Willem Jacob van der Burg, Heesch, Netherlands

[73] Assignee: Akzona Incorporated, Asheville, N.C.

[21] Appl. No.: 649,434

[22] Filed: Jan. 15, 1976

Related U.S. Application Data

[62] Division of Ser. No. 463,712, April 24, 1974, Pat. No. 3,966,723.

[30] Foreign Application Priority Data

Apr. 26, 1973 Netherlands .................... 7305811

[51] Int. Cl.² .................... C07D 471/04
[52] U.S. Cl. .................... 260/293.55; 260/268 PC; 260/243.3
[58] Field of Search ........... 260/247.5 G, 268 PC, 260/293.55, 247.1 L

[56] References Cited
U.S. PATENT DOCUMENTS 3,950,425   4/1976   van der Burg .................... 260/576

Primary Examiner—Henry R. Jiles
Assistant Examiner—R. W. Ramsuer
Attorney, Agent, or Firm—Francis W. Young; Charles A. Wendel

[57] ABSTRACT

The invention discloses novel compounds of the general formula:

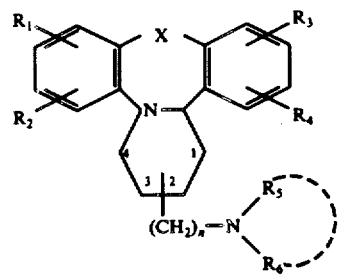

and salts thereof, in which the amino(alkyl) moiety is present at position 2 or 3 and in which X stands for oxygen, sulphur, the group >NR₇ or the group —CR₈R₉—;

$R_1$, $R_2$, $R_3$ and $R_4$ represent hydrogen, hydroxy, halogen, alkyl (1–6 C), alkoxy (1–6 C), alkylthio (1–6 C) or trifluoromethyl;

$R_5$ and $R_6$ represent hydrogen, alkyl (1–6 C), aralkyl (7–10 C) or together in combination with the nitrogen atom a heterocyclic five- or six-membered ring;

$R_7$ stands for hydrogen or alkyl (1–4 C);

$R_8$ and $R_9$ stand for hydrogen or methyl and is the number 0, 1, 2 or 3, having valuable central nervous system (CNS) activities, especially antidepressant activity.

5 Claims, No Drawings

HEXAHYDRO PYRIDINE [1,2D] DIBENZA [B,F] (1,4)-DIAZEPINES

CROSS REFERENCE TO RELATED APPLICATION

This application is a division of application Ser. No. 463,712, filed Apr. 24, 1974, now U.S. Pat. No. 3,966,723, issued June 29, 1976.

The present invention relates to novel biologically active amino-substituted piperidino-derivatives and to processes for the preparation thereof.

It was found that compounds of the general formula I:

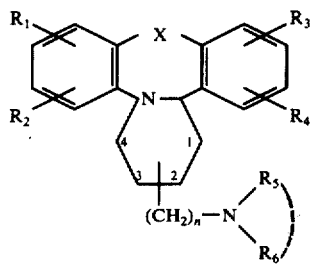

as well as the pharmaceutically acceptable salts thereof, whereby the

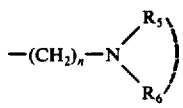

moiety is present at position 2 or 3 and in which

X stands for oxygen, sulphur, the group $>NR_7$ or the group $-CR_8R_9-$;

$R_1$, $R_2$, $R_3$ and $R_4$ represent hydrogen, hydroxy, halogen, alkyl (1-6 C), alkoxy (1-6 C), alkylthio (1-6 C) or trifluoromethyl;

$R_5$ and $R_6$ represent hydrogen, alkyl (1-6 C), aralkyl (7-10 C) or together in combination with the nitrogen atom a heterocyclic five- or six-membered ring;

$R_7$ stands for hydrogen or alkyl (1-4 C);

$R_8$ and $R_9$ stand for hydrogen or methyl and $n$ is the number 0, 1, 2 or 3, possess valuable C.N.S. activities. The toxicity of these compounds is exceedingly low.

The compounds according to the invention may be prepared in a manner commonly used for analogous compounds.

A very easy starting point for the synthesis of the compounds in question is a compound of the general formula II:

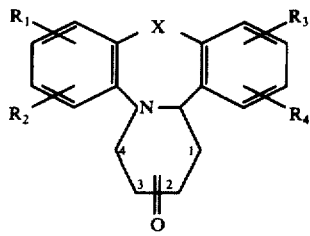

in which the ketogroup is present at position 2 or position 3 and in which $R_1$, $R_2$, $R_3$, $R_4$ and X have the meanings mentioned above. The compounds II are, as far as known, novel compounds.

The starting material II can be prepared in various manners. The most simple method to prepare the compound II is the condensation of vinylmethylketone

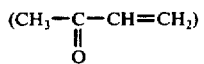

with a derivative of morphanthridine, dibenzooxazepine, dibenzothiazepine or dibenzodiazepine of the general formula III:

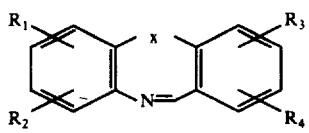

in which $R_1$, $R_2$, $R_3$, $R_4$ and X have the meanings mentioned above. In this condensation reaction the 2-keto compound II is obtained in a fairly good yield.

The 3-keto compound of formula II may be prepared from the corresponding 2-keto-compound II in a conventional manner. For example, the 2-keto compound is converted into the corresponding 2-keto-3-hydroxyimino compound with isoamylnitrite and potassium in tert.butanol (see reaction scheme 4 at page 5), after which the carbonyl group at position 2 is reduced by means of a Wolff-Kishner reduction and the 3-hydroxyimino moiety in the compound thus obtained saponified under acidic conditions or with the aid of sodiumbisulfite in an alcohol/water mixture.

Starting from a compound with formula II the endproducts according to formula I can be prepared in various manners. All these routes are known per se and are standard procedures commonly used for their preparation of similar compounds.

In principle, the amino(alkyl)compounds of the invention are prepared starting from the 2- or 3-keto compound II by two different approaches, namely the amino(alkyl)group can be introduced into the position adjacent to the keto group, or the keto-group itself can be converted into the amino (alky)group desired. In the first approach a 3-amino(alkyl)comound I is prepared from a 2-keto-compound II or a 2-amino(alkyl)compound I is prepared from a 3-keto-compound II; in the second approach a 2-amino(alkyl)compound I is prepared from a 2-keto compound II or a 3-amino(alkyl) compound I is prepared from a 3-keto compound II.

The endproducts according to formula I may be manufactured, for example, by reducing the carbonyl group of a compound of the general formula: IV A or IV B.

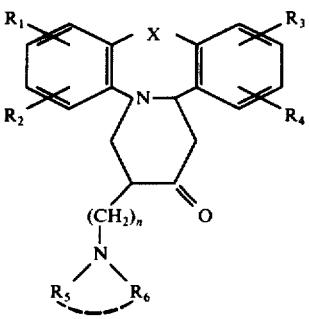

or

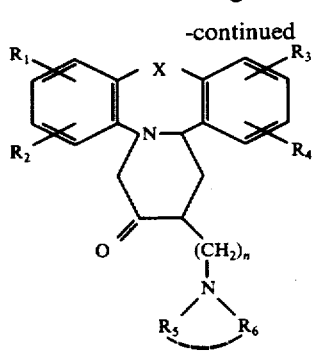

or a salt thereof, in which $R_1$, $R_2$, $R_3$, $R_4$, $R_5$, $R_6$ $n$ and $\zeta$ have the meanings afore-mentioned.

This reduction from $>C=O$ to $>CH_2$ is performed in a way usual for similar reductions, for example by means of a Wolff-Kishner, Huang-Minlon or Clemmensen reduction or by hydrogenolysis of di-alkylthio-acetals that are prepared from the relative keto-compound IV.

Besides the use of the compounds IV A and IV B as intermediates in the synthesis for the preparation of the compounds according to the general formula I, these compounds (IV A and IV B) can also be applied as biologically active substances. Like the compounds of formula I, they have C.N.S. in particular antidepressant activities. The compounds IV A and IV B can be administered both orally and parenterally, preferably in a daily dose of 0.01–10 mg per kg body weight.

The compound IV required in the above-mentioned synthesis can be prepared from the starting product II in various ways. By way of example a number of reaction schemes, given on the next page, illustrate the preparation of a compound IV starting from a compound II in which the keto group is at position 2. For compounds II with the keto group at position 3 these reactions proceed in an identical way.

1. 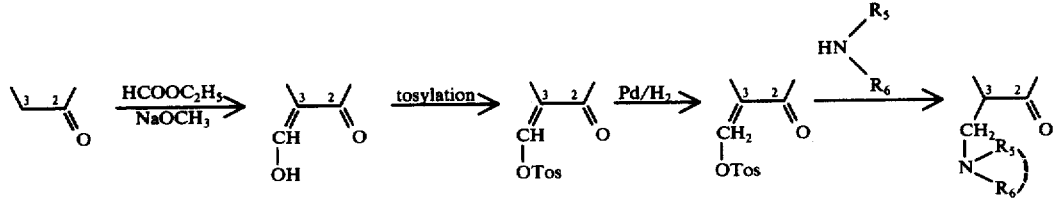

2. 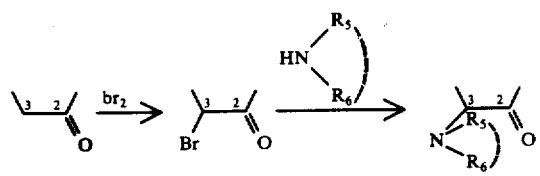

3. 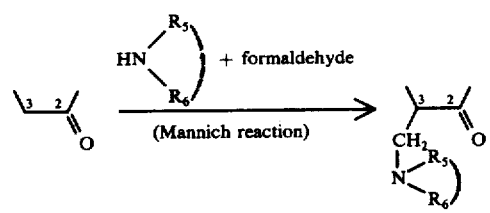

4. 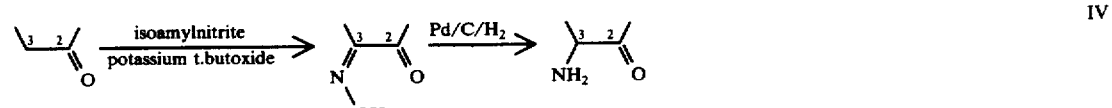

5. 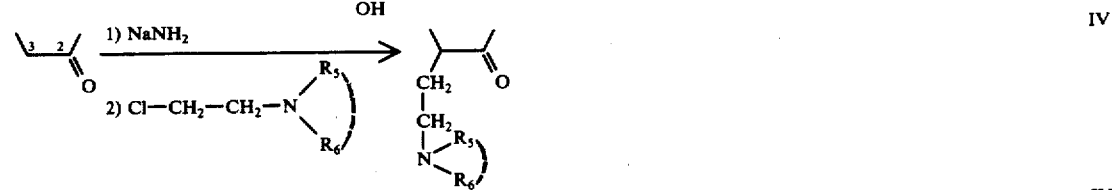

6. 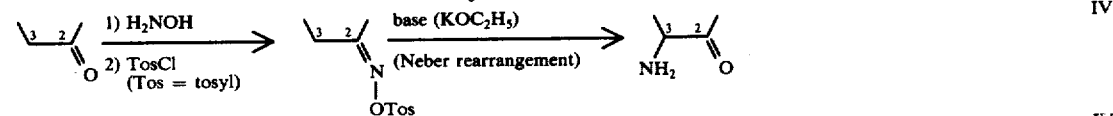

7. 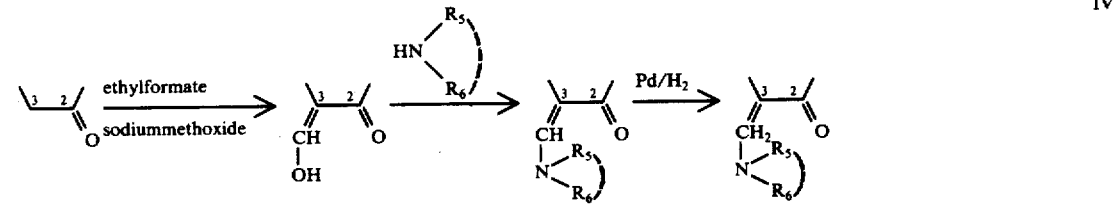

It will be clear that the steps mentioned in these reaction schemes for preparing starting product IV need not necessarily be carried out in this strict sequence to obtain the endproduct according to formula I.

Thus the Wolff-Kishner reduction (keto group reduction to —CH₂), to which compound IV in reacton scheme 4 would have to be subjected to obtain the endproduct according to formula I, can also be performed at an earlier stage, especially on the 2-keto-3-oxime compound (scheme 4). Further it is possible to have the reduction of the double bond (position 3) in reaction scheme 1 or 7 performed at an earlier or later stage of the synthesis to the endproduct I.

These and other obvious modifications in the reaction scheme are, without being claimed apart, considered to be fully analogous to the route claimed.

The conversion of a 2- or 3-keto compound II into a compound according to formula I having the amino(alkyl) group at the same position as the keto group of the starting material II may be carried out in various manners. All these methods are conventional methods, already described for similar compounds.

The method, which can generally be used in preparing the compounds I of the invention, consists of the condensation of a compound with the general formula V:

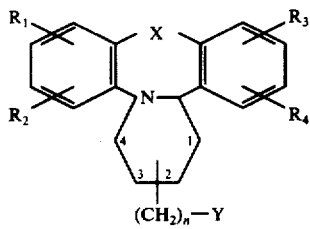

in whih the —(CH₂)ₙ—Y group is present at position 2 or 3, R₁, R₂, R₃, R₄, n and X have the meanings specified before and Y represents a suitable leaving group, such as halogen, or an etherified or esterified hydroxyl group, with ammonia or an amine according to the general formula VI:

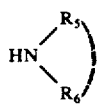

or an acid addition salt thereof, in which R₅ and R₆ have the meanings defined previously.

Leaving groups are well defined groups, described in various chemical handbooks.

Suitable leaving groups for this condensation reaction are for example a tosyloxy group, a mesyloxy group, a p-bromophenyl-sulphonyloxy group, a chlorine, bromine or iodine atom.

The compound V required for this condensation reaction may be prepared from the starting material II described before by reducing the keto group to a hydroxyl group, for instance by catalytic hydrogenation or with metal hydrides such as LiAlH₄NaBH₄ or diboran, followed by converting this hydroxyl group into the desired leaving group in a conventional manner, for instance by tosylation, mesylation, reaction with SOCl₂, PCl₅, PBr₃, etc.

Extension of the alkyl chainlength (from n=0 to n=1, 2 or 3) can be performed in the usual way, for instance by treating a compound V, in which n=0 with a cyanide such as potassium- or sodiumcyanide. The cyanogroup in the compound thus obtained can either be reduced to the corresponding aminomethyl group or be hydrolysed to the corresponding carboxyl group. The aminomethyl compound is then treated with nitrous acid at low temperature (Piria), whereas the carboxyl compound is reduced. Both reactions afford the hydroxy-methyl compound in fairly good yields. Finally the hydroxymethyl compound thus obtained is converted into a compound in which the hydroxyl group is replaced by a leaving group.

By repeating the above-mentioned reaction steps, a further extension of the alkyl chain is obtained.

The compounds I in question can further be prepared by reduction of the cyanide or azide group of compounds with the general formula VII:

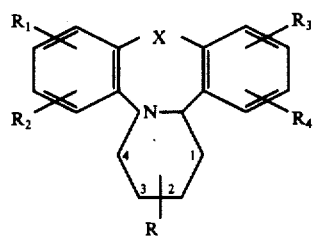

in which R is present at position 2 or 3, representing one of the following moieties: —(CH₂)ₙ₋₁—CN or —(CH₂)ₙ—N₃, and in which R₁, R₂, R₃, R₄, X and n have the meanings indicated before.

The reduction is performed in the usual way for this kind of compounds. The cyanide group is preferably reduced by means of metalhydrides, especially lithium-aluminium-hydride, the azide group by a metalhydride such as LiAlH₄ or NaBH₄ or by hydrogenation in the presence of a metal catalyst such as palladium, Raney nickel, etc.

The starting materials with formula VII required in this method can, for example, be prepared by treating a compound of formula V with sodiumcyanide or sodiumazide, or by treating a compound II with HCN, eliminating the hydroxy group and reducing the double bond formed, possibly together with —CN or —N₃.

A simple and direct method in preparing the compound I (with n = 0) consists of the reaction of the starting material II with the amine according to formula VI in the presence of a reducing agent, such as formic acid, metal hydrides such as LiAlH₄, NaBH₄, Na(CN)BH₃, etc. or by means of hydrogen, if required in the presence of a catalyst, such as palladium, platina, palladium on charcoal, nickel etc.

This reductive amination is well-known in organic chemistry and described in any chemical handbook.

The compounds of the invention (with n = 0) can further be prepared by reduction of a compound of the general formula VIII:

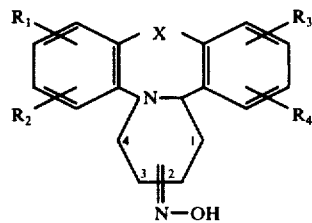

whereby the oxime group is present at position 2 or 3 and in which $R_1$, $R_2$, $R_3$, $R_4$ and X have the meanings indicated before.

This reduction is performed in the way as usual for reduction of an oxime, for instance with sodium or sodium-amalgam alcohol, by hydrogenation preferably in the presence of a metal catalyst, or with metalhydrides such as $LiAlH_4$.

The compound VIII is prepared direct from the corresponding keto compound II by treating the latter with hydroxylamine in the usual way, or indirect from the keto compound II by reacting it with isoamylnitrite/-potassium-t.butoxide, followed by a Wolff-Kishner reduction of the keto group (see reaction scheme 4 on page 5).

A very convenient method for the preparation of the compounds I with $n > 1$ is the reduction of an amide of the general formula IX:

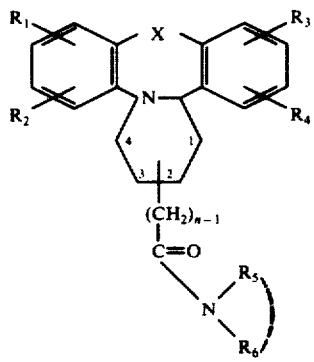

IX in which the amide-side chain is present at position 2 or 3 and $R_1$, $R_2$, $R_3$, $R_4$, $R_5$, $R_6$, X and $n$ have the meanings defined previously.

The reduction is carried out in a conventional manner for the reduction of amides, for example with metalhydrides, especially $LiAlH_4$.

The starting compounds IX for this reduction can be prepared by hydrolysis of the cyano-compound of the general formula VII, yielding the corresponding carboxyl compound, which compound is converted into the corresponding amide in the usual way, for example by halogenating the carboxyl group affording the acid halide, followed by reacting the acid halide with an amine of the formula VI. The primary amide of formula IX may, of course, be prepared directly by partial hydrolysis of the cyano-compound VII.

Finally the present compounds of the invention with general formula I may be prepared by a reduction of a compound with the general formula X:

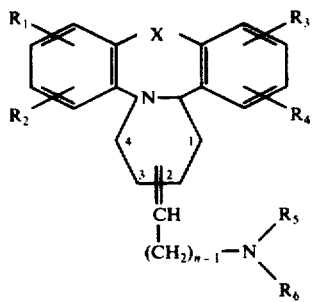

X in which the aminoalkylidene sidechain is present at position 2 or 3 and in which $R_1$, $R_2$, $R_3$, $R_4$, $R_5$, $R_6$, X and $n$ have the meanings mentioned previously.

This reduction is carried out in the usual manner, for example, by hydrogenation in the presence of a catalyst such as palladium, palladium on charcoal, Raney nickel etc.

The starting compounds X for this reduction can be prepared quite easily starting from the keto compound II by means of a Wittig reaction with the aid of the reagent:

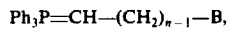

in which $n$ has the aforesaid meaning, Ph generally represents an aryl, in particular a phenyl group and B stands for an amino group

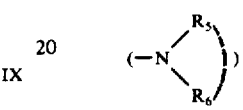

or for a group which can be converted into an amino group, such as a carboxyl group, a carbonyl group, a hydroxy group or a cyanide group.

A very simple method for the preparation of a compound X with $n = 2$ consists of the reaction of the keto compound II with acetonitril in the presence of, for instance, sodiumethoxide, followed by reduction of the cyano group in the compound thus obtained. If necessary the reduction of the cyano group and the reduction of the double bond can take place simultaneously, cq. by catalytic hydrogenation (Raney nickel) or with diboran.

The starting material II contains an asymmetric carbon which means that besides the racemate II also the separate optical antipodes can be used as starting material.

By converting the starting product II into the amine according to the invention a second asymmetric centre is introduced. This asymmetric centre leads to compounds, in which the amino(alkyl)-substituent at position 2 or 3 of the molecule is in equatorial or axial position, or to a mixture of both types of compounds.

In general the above-mentioned methods in preparing the compounds I ($n = 0$), starting from the starting material II, are resulting in compounds, in which the amino-substituent is substantially in the equatorial position. Only in the case that a leaving group is used in one of the aforesaid methods, generally an inversion occurs so that mainly the axial position is obtained.

A mixture of compounds I having the amino(alkyl) substituent in equatorial and axial position can, if desired, be separated very easily, for instance by column chromatography, or in many cases by mere crystallization as HCl salt or another acid addition salt.

The pharmaceutically acceptable salts of the compounds I according to the invention are acid addition salts and quaternary ammonium compounds.

The novel compounds according to the invention may be isolated from the reaction mixture in the form of a pharmaceutically acceptable acid addition salt, dependent upon the conditions in which the reaction is carried out. The acid addition salts may also be obtained by treating the free base with a pharmaceutically acceptable organic or inorganic acid. Acids that can be used in this connection are: hydrochloric acid, hydrobromic acid or hydroiodic acid, phosphoric acid, acetic acid, propionic acid, glycollic acid, maleic acid, malonic acid, succinic acid, tartaric acid, citric acid, ascorbic acid, salicylic acid or benzoic acid.

The quaternary ammonium compounds and in particular the lower (1-4 C) alkyl quaternary ammonium compounds are obtained by reacting the compounds of the general formula I with an alkyl halide, for example methyl iodide or methyl bromide.

It is possible as a matter of course to introduce or to modify the substituents at one or both phenyl nucleii even after the condensation reactions described before. Thus a hydroxyl group can be converted into an alkoxy group, an amino group into a hydroxy- or halogen group, a methoxy group into a hydroxy group etc.

The unsubstituted or monosubstituted amines of the general formula I ($R_5$ and/or $R_6$ = H) may be alkylated in the usual way, for example by reaction with an alkyl- or aralkylhalide. More common for this purpose is, however, the acylation of the nitrogen atom in question with, for example, an acid chloride or anhydride followed by a reduction of the carbonyl group of the N-acyl derivative thus obtained. For the introduction of methyl groups at the nitrogen atom the procedure according to Eschweiler-Clarke (heating with a mixture of formaldehyd and formic acid) or the reaction with formaldehyde and sodiumcyanoborohydride in a suitable solvent, such as acetonitril, is preferred.

With an alkyl group with 1-6 carbon atoms is meant a branched or unbranched alkyl group such as methyl, ethyl, propyl, isopropyl, butyl, isobutyl, tert.butyl, n.pentyl, isopentyl and hexyl.

The alkyl group in the alkoxy and alkylthio moieties has the same meaning.

An aralkyl group mentioned in the definition and $R_5$ and $R_6$ is preferably a phenylalkyl group, in which the alkyl group contains 1-4 carbon atoms, such as benzyl, phenylethyl, phenylpropyl, phenylisopropyl, phenylbutyl and phenylisobutyl.

The heterocyclic 5- or 6-membered ring (definition of $R_5$ and $R_6$) may either be saturated or unsaturated, such as a pyrrolino group, a pyrrolidino group, a piperidino group, an oxazolidino group, a morpholino group, a piperazino group, etc.

Amines according to the general formula VI, that may be used in the various condensation reactions to obtain the compounds of the invention, are, for example ammonia, methylamine, dimethylamine, diethylamine, isopropylamine, dibutylamine, t.butylamine, benzylamine, phenylethylamine, phenylpropylamine, 2-phenyl-1-methyl-ethylamine, pyrroline, pyrrolidine, piperidine, oxazolidine, morpholine, piperazine, etc.

As already pointed out previously the compounds of the invention I exert a valuable central nervous system activity. This C.N.S. activity can be concluded from the results of various pharmacological experiments, such as the reserpine antagonism test, reserpine reversal test, aggression isolated mice test, ambulation test, rotarod test, grip strength test, muricidal inhibition test, etc.

The surprising high activity of the compounds I in antagonizing hypothermia induced by reserpine (reserpine antagonism test) give strong indications that the present compounds can be used as antidepressants.

The compounds I may be administered both orally and parenterally, preferably in a daily dose of from 0.1 to 10 mg per kg bodyweight.

Mixed with suitable auxiliaries the present compounds can be compressed into solid dosage units such as pills, tablets or coated tablets, or they can be processed into capsules. With the aid of suitable liquids the compounds can be applied as injection preparations in the form of solutions, emulsions or suspensions.

Preferably compounds I are used in which X stands for a methylene moiety (—$CH_2$—) or a >N-alkyl moiety, in particular, a >N—$CH_3$ moiety. Especially the latter type of compounds (X = >N-alkyl) excels in a very potent anti-depressant activity.

Furthermore the compounds I, in which n is 0 or 1 are to be preferred over the compounds I, having a longer side chain (n = 2 or 3).

In the Examples the following nomenclature has been used:

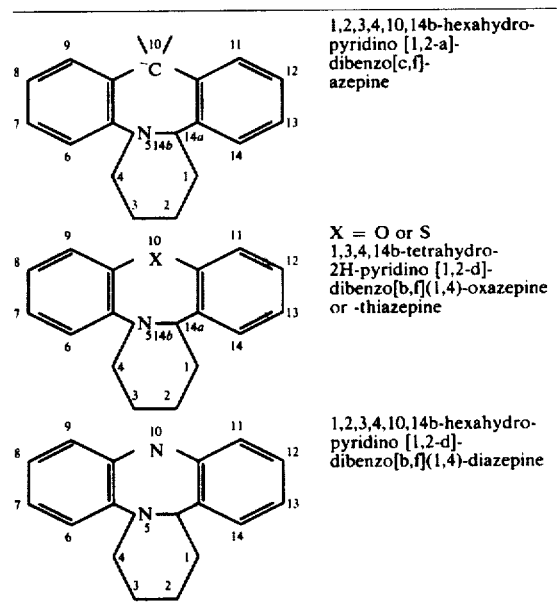

1,2,3,4,10,14b-hexahydro-pyridino [1,2-a]-dibenzo[c,f]-azepine

X = O or S
1,3,4,14b-tetrahydro-2H-pyridino [1,2-d]-dibenzo[b,f](1,4)-oxazepine or -thiazepine 1,2,3,4,10,14b-hexahydro-pyridino [1,2-d]-dibenzo[b,f](1,4)-diazepine By way of example the preparation of various starting products are disclosed. The preparation of analogous starting products proceeds in exactly the same way.

STARTING PRODUCTS

1. Preparation 2-keto-compounds according to general formula II

A. 2-keto-1,2,3,4,10,14b-hexahydro-pyridino[1,2,-a]-dibenzo[c,f]-azepine

To a solution of 100 g of morphanthridine in 2.5 liters of benzene are added 100 ml of methylvinylketon. The mixture is then refluxed. To the boiling solution are added dropwise 50 ml of a solution of 35% HCl in ethanol, after which the solution is refluxed for another 15 hours. After cooling of the mixture the benzene layer is washed with 500 ml of water (3×) and then evaporated in vacuo. The residue is recrystallized from ethanol.

Obtained in this manner: 44 g with a melting point of 140°-142° C.

Rf in toluene: ethylacetate (9:1) = 0.80 on $SiO_2$.

In the same way as described under A are prepared:

B. 2-keto-8-bromo-1,2,3,4,10,14b-hexahydro-pyridino[1,2,-a]-dibenzo[c,f]-azepine; melting point 183°-185 C.

C. 2-keto-8-chloro-1,2,3,4,10,14b-hexahydro-pyridino[1,2,-a]-dibenzo[c,f]-azepine; melting point 144°-147° C.

D. 2-keto-11,12-dimethyl-1,2,3,4,10,14b-hexahydro-pyridino [1,2-a]-dibenzo[c,f,]-azepine (oil). Rf in toluene-ethylacetate (9:1) = 0.85 on SiO$_2$.

E. 2-keto-8-hydroxy-1,2,3,4,10,14-b-hexahydro-pyridino[1,2-a]-dibenzo[c,f]-azepine; (oil). Rf in toluene = 0.60 on SiO$_2$.

F. 2-keto-8-methoxy-1,2,3,4,10,14b-hexahydro-pyridino[1,2-a]-dibenzo[c,f]-azepine (oil). Rf in toluene:ethylacetate (8:2) = 0.78 on SiO$_2$.

G. 2-keto-7-chloro-1,2,3,4,14b-tetrahydro-2H-pyridino[1,2-d]-dibenzo[b,f](1,4)-thiazepine (oil). Rf in toluene:ethylacetate (8:2) = 0.75 on SiO$_2$.

H. 2-keto-7-trifluoromethyl-1,3,4,14b-tetrahydro-2H-pyridino [1,2-d]-dibenzo[b,f](1,4)-thiazepine (oil) Rf in toluene:ethylacetate (9:1) = 0.90 on SiO$_2$.

I. 2-keto-13-methyl-1,3,4,14b-tetrahydro-2H-pyridino[1,2-d]-dibenzo[b,f](1,4)-thiazepine; melting point 104°-107° C.

K. 2-keto-7-methyl-1,3,4,14b-tetrahydro-2H-pyridino[1,2-d]-dibenzo[b,f](1,4)-oxazepine; melting point 105°-107° C.

L. 2-keto-11-methyl-1,3,4,14b-tetrahydro-2H-pyridino[1,2-d]-dibenzo[b,f](1,4)-oxazepine; melting point 164°-166° C.

M. 2-keto-7,11-dimethyl-1,3,4,14b-tetrahydro-2H-pyridino [1,2,-d]-dibenzo[b,f](1,4)-oxazepine; (oil) Rf in toluene:ethylacetate (8:2) = 0.70.

N. 2-keto-10-methyl-1,2,3,4,10,14b-hexahydro-pyridino[1,2-d]-dibenzo[b,f] (1,4)-diazepine; melting point 176°-178° C.

P. 2-keto-10-methyl-13-methoxy-1,2,3,4,10,14b-hexahydropyridino[1,2-d]-dibenzo[b,f](1,4)-diazepine; melting point 127°-128° C.

Q. 2-keto-1,3,4,14b-tetrahydro-2H-pyridino[1,2-d]-dibenzo [b,f](1,4)-oxazepine; melting point 101°-103° C.

2. Preparation 3-keto-compounds according to formula II

A. 3-keto-1,2,3,4,10,14b-hexahydro-pyridino[1,2-a]-dibenzo[c,f]-azepine 2.6 g of 2-keto-1,2,3,4,10,14b-hexahydro-pyridino[1,2-a]-dibenzo[c,f]-azepine are added under nitrogen atmosphere to a solution of 3.9 g of potassium in tertiary butanol. The mixture is stirred for 10 hours while every 2 hours 4 ml of isoamylnitrite are added (the total quantity of isoamylnitrite is 20 ml).

After that the mixture is filtered and the precipitate (2-keto-3-oxime compound) washed with t.butanol and ether. The product is then added to 17 ml of diethyleneglycol after which 5 ml of hydrazinehydrate and 2 g of KOH are added and the mixture obtained is heated at 160° C for 4 hours.

The reaction mixture is poured into water whereafter the precipitated oxim is filtered off.

Yield of the 3-oxim: 2.0 g. The oxime is refluxed in a mixture of 20 ml of water, 20 ml of ethanol and 4 g of sodium bisulphite for 2.5 hours. The alcohol is then distilled off and the remaining solution is extracted into ether. The ether layer is evaporated to dryness.

Yield of the 3-keto compound: 1.8 g. (oil).
Rf in toluene:ethylacetate (9:1) = 0.70.
In the same way are prepared:

B. 3-keto-8-bromo-1,2,3,4,10,14b-hexahydro-pyridino[1,2-a]-dibenzo[c,f]-azepine Rf in toluene = 0.15 on SiO$_2$.

C. 3-keto-7-trifluoromethyl-1,3,4,14b-tetrahydro-2H-pyridino [1,2-d]-dibenzo[b,f](1,4)-thiazepine Rf in toluene:ethylacetate (9:1) = 0.90.

D. 3-keto-11-methyl-1,3,4,14b-tetrahydro-2H-pyridino[1,2-d]-dibenzo[b,f](1,4)-oxazepine Rf is toluene:ethylacetate (8:2) = 0.75.

E. 3-keto-10-methyl-1,2,3,4,10,14b-hexahydro-pyridino[1,2-d]-dibenzo-[b,f](1,4)-diazepine Rf in toluene:ethylacetate (9:1) = 0.90 Rf in hexane;acetone (9:1) = 0.20.

3.
2-hydroxy-1,2,3,4,10,14b-hexahydro-pyridino[1,2-a]-dibenzo[c,f]-azepine

To a suspension of 10 g of LiAlH$_4$ in 800 ml of dry ether is added to solution of 30 g of 2-keto-1,2,3,4,10,14b-hexahydro-pyridino[1,2-a]-dibenzo[c,f]-azepine in 1 liter of ether/THF mixture (7:3). The suspension obtained is heated while stirring for 30 minutes.

After cooling the mixture 40 ml of water are added carefully so as to decompose the excess of LiAlH$_4$, after which the solution is filtered off and the filtrate is evaporated and recrystallized. Obtained in this manner: 25 g; melting point 146°-147° C. (equatorial).

Rf in toluene:ethylacetate (8:2) = 0.25.

4.
2-tosyloxy-1,2,3,4,10,14b-hexahydro-pyridino[1,2-a]-dibenzo[c,f]-azepine 4 g of the 2-hydroxy compound from 3 are dissolved in 50 ml of dry pyridine. This solution is cooled on ice and then 5 g of tosylchloride is added while stirring.

After left to stand the solution for 24 hours at room temperature it is poured into 400 ml of water. After that the aqueous solution is extracted into ether, the ether layer is washed with 2N hydrochlorid acid and then with water. After this the ether layer is dried and evaporated to dryness.

Obtained in this manner: 5 g; melting point 130°-132° C (equat.).

Rf is hexane-acetone (95:5) = 0.45 on SiO$_2$; in toluene; 0.31.

5.
2-cyano-1,2,3,4,10,14b-hexahydro-pyridino[1,2-a]-dibenzo[c,f]-azepine 4.6 g. of the compound obtained in 4 are dissolved in 50 ml of dimethylsulfoxide, after which 2 g of micropowdered NaCN are added. The mixture is heated while stirring at 90° C for 2 hours. After cooling the mixture it is poured into 300 ml of water yielding a light yellow precipitate. This precipitate is dried.

Obtained in this manner: 2.2 g; melting point 184°-186° C (axial.).

Rf in hexane:acetone (95:5) = 0.60 on SiO$_2$.

6.
2-azido-1,2,3,4,10,14b-hexahydro-pyridino[1,2-a]-dibenzo[c,f]-azepine

To 4.5 g of the compound obtained in 4, dimethylformamide (25ml) are added and after that 1.5 g of activated sodium-azide. the mixture is refluxed for 5 hours, after which this mixture is poured into water and extracted into ether, whereafter the ether layers are dried and evaporated to dryness.

The precipitate is immediately used for further conversions.

Rf in hexane:acetone (9:1) = 0.65 on SiO$_2$ (axial position).

7.
2-cyanomethylidene-1,2,3,4,10,14b-hexahydro-pyridino[1,2-a]-dibenzo[c,f]-azepine 1 of 2-keto-1,2,3,4,10,14b-hexahydro-pyridino[1,2-a]-dibenzo[c,f]-azepine is mixed with 1 ml of benzene, 0.5 ml of acetonitril and 0.5 g. of molecular sieve (4 A). 50 mg of sodium-ethoxyde are added and the mixture is heated for 3 hours (90°-100° C). After cooling the mixture the molecular sieve is filtered off and the filtrate evaporated. The precipitate is recrystallized from ethanol.

Obtained in this manner: 200 mg; melting point 215°-217° C.

8.
2-carboxy-1,2,3,4,10,14b-hexahydro-pyridino[1,2-a]-dibenzo[c,f]-azepine (axial.)

1.1 g of the 2-cyano-compound obtained in 5 and 55 ml concentrated HCl solution are heated in a sealed ampoule for 4 hours. The precipitate formed is filtered off and dried. Yield: 8.6 g of the HCl salt of the title compound; melting point 260°-163° C.

Dissolving this salt in 2 n NaOH and treating the alkaline solution with 0.1 n HCl to neutral yields a precipitate of the free base, which is filtered off and dried. Yield:

5.1 g; melting point 207°-209° C.

Rf is toluene:ethanol (8:2) = 0.55 on SiO$_2$.

EXAMPLE I

Preparation
2-amino-1,2,3,4,10,14b-hexahydro-pyridino[1,2-a]-dibenzo[c,f]-azepine 15 g of 2-keto-1,2,3,4,10,14b-hexahydro-pyridino[1,2-a]-dibenzo[c,f]-azepine are dissolved in 500 ml of ethanol. To this solution are added 5 g of hydroxylamine.HCl and 10 ml of pyridine. The solution is then heated on a vapour-bath for 1 hour, after which the solution is evaporated dryness in vacuo. The precipitate is added to ether and washed with a diluted acid. The ether layer is washed with water once more and after that evaporated to dryness. Yield of the corresponding 2-oxim compound: 18 g (oil).

Rf in toluene:ehtylacetate (8:2) = 0.45.

600 mg of this oxime is dissolved in 30 ml of isopropanol, after which 2 g of sodium are added to the solution. The mixture is heated until all sodium has been dissolved. After cooling the solution it is poured into 300 ml of water and extracted with ether. The ether layer is evaporated to dryness and the precipitate is recrystallized from ethanol.

Melting point: 58°-61° C (position NH$_2$ group: equatorial).

Melting point of the hydrochloride: 223°-226° C (equatorial).

Rf is methanol:acetone (9:1) = 0.15.

EXAMPLE II

In the same way as described in example I are prepared by reduction of the corresponding 2- or 3-oxim compound:

2-amino-8-bromo-1,2,3,4,10,14b-hexahydro-pyridino[1,2-a] -dibenzo[c,f]-azephine (oil); Rf in methanol:acetone (9:1) = 0.10.

2-amino-8-methoxy-1,2,3,4,10,14b-hexahydro-pyridino[1,2-a]-dibenzo[c,f]-azepine; Rf in methanol:acetone (85:15) = 0.15 on SiO$_2$.

2-amino-13-methyl-1,3,4,14b-tetrahydro-2H-pyridino[1,2-d]-dibenzo[b,f](1,4)-thiazepine (oil); Rf in methanol:acetone (9:1) = 0.12 on SiO$_2$.

2-amino-7-trifluoromethyl-1,2,3,14b-tetrahydro-2H-pyridino [1,2-d]-dibenzo[b,f](1,4)-thiazepine (oil); Rf in chloroform:methanol (8:2) = 0.30.

2-amino-7-chloro-10-methyl-1,2,3,4,10,14b-hexahydro-pyridino [1,2-d]-dibenzo[b,f](1,4)-diazepine (oil).

2-amino-1,2,3,14b-tetrahydro-2H-pyridino[1,2-d]-dibenzo[b,f](1,4)-oxazepine; Melting point HCl salt: 230°-235° (dec.).

2-amino-10-methyl-13-methozy-1,2,3,4,10,14b-hexahydro-pyridino [1,2-d]-dibenzo[b,f](1,4)-diazepine (oil); Rf in methanol:acetone (8:2) = 0.20 on SiO$_2$.

3-amino-1,2,3,4,10,14b-hexahydro-pyridino[1,2-a]-dibenzo[c,f]-azepine; melting point HCl salt: 220°-225° C (dec.).

3-amino-11-methyl-1,2,3,14b-tetrahydro-2H-pyridino[1,2-d]-dibenzo[b,f](1,4)-oxazepine (oil).

2-amino-7-hydroxy-10-methyl-1,2,3,4,10,14b-hexahydro-pyridino [1,2-d]-dibenzo[b,f](1,4)-diazepine (oil).

EXAMPLE III

Preparation
2-methylamino-1,2,3,4,10,14b-hexahydro-pyridino[1,2-a]-dibenzo[c,f]-azepine 1 g of 2-keto-1,2,3,4,10,14b-hexahydro-pyridino[1,2-a]-dibenzo[c,f]-azepine is dissolved in 100 ml of ethanol, after which 10 ml of methylamine and 200 mg of palladium (10%) on charcoal are added. Then hydrogen is passed through this mixture until no hydrogen is absorbed any longer.

The mixture is filtered and the filtrate is evaporated and recrystallized from ethanol.

Obtained in this manner: 0.9 g (oil).

Rf in methanol:acetone (9:1) = 0.15 on SiO$_2$.

Melting point as fumarate: 185°-187° C (equatorial position).

By taking instead of methylamine one of the following reagents, namely ethylamine, isopropylamine, morpholine or piperidine the following compounds are obtained:

2-ethylamino-1,2,3,4,10,14b-hexahydro-pyridino[1,2-a]-dibenzo[ c,f]-azepine, 2-isopropylamino-1,2,3,4,10,14b-hexahydro-pyridino[1,2-a]-dibenzo[c,f]-azepine, 2-morholino-1,2,3,4,10,14b-hexahydro-pyridino[1,2-a]-dibenzo[c,f]-azepine, 2-piperidino-1,2,3,4,10,14b-hexahydro-pyridino[1,2-a]-dibenzo[c,f]-azepine.

EXAMPLE IV

2-dimethylamino-1,2,3,4,10,14b-hexahydro-pyridino[1,2-a]-dibenzo[c,f]-azepine 20 g of 2-keto-1,2,3,4,10,14b-hexahydro-pyridino[1,2-a]-dibenzo[c,f]-azepine are suspended in 600 ml of ethanol. To this mixture are added 25 ml of dimethylamine and 2 g of palladium (10%) on charcoal. The mixture is hydrogenated until no hydrogen is absorbed anymore.

After this the catalyst is filtered off, the filtrate evaporated and the precipitate recrystallzed from ethanol.

Obtained in this manner: 16 q.

Melting point free base 88°–89° C (equatorial), melting point

HCl salt 266°–269° C (equatorial). Rf in methanol:acetone (9:1) = 0.20 on $SiO_2$.

Treatment of the free base with methyljodide yields the iodomethylate; melting point 202°–205° C.

By having the keto compound first reacted with dimethylamine at low temperature, e.g. at 0° C, in the presence of a Lewis acid, such as $TiCl_4$, $AlCl_3$, etc. the enamine formed as intermediate-product can be isolated and reduced afterwards.

EXAMPLE V

In the same manner as described in example IV the following compounds are prepared starting from the corresponding 2- or 3-keto compound:

2-dimethylamino-8-bromo-1,2,3,4,10,14b-hexahydro-pyridino[1,2-a]-dibenzo[c,f]-azepine (oil); Rf in methanol:acetone (8:2) = 0.20 on $SiO_2$ (equatorial).

2-dimethylamino-13-methyl-1,3,4,14b-tetrahydro-2H-pyridino[1,2-d]-dibenzo[b,f](1,4)-thiazepine; melting point 141°–143° C, melting point of the maleate salt: 192°–195° C (equatorial).

2-dimethylamino-8-methoxy-1,2,3,4,10,14b-hexahydro-pyridino[1,2-a]-dibenzo[c,f]-azepine (oil); Rf in methanol:acetone (8:2) = 0.25 on $SiO_2$ (equatorial).

2-dimethylamino-7-trifluoromethyl-1,3,4,14b-tetrahydro-2H-pyridino[1,2-d]-dibenzo[b,f](1,4)-thiazepine (oil); Rf in chloroform:methanol (8:2) = 0.45 on $SiO_2$ (eq.).

2-dimethylamino-7-chloro-1,3,4,14b-tetrahydro-2H-pyridino[1,2-d]-dibenzo[b,f](1,4)-thiazepine; melting point free base 63°–68° C (equatorial).

2-dimethylamino-11-methyl-1,3,4,14b-tetrahydro-2H-pyridino[1,2-d]-dibenzo[b,f](1,4)-oxazepine; melting point free base 111°–113° C (eq.); melting point HCl salt 263°–265° C (eq.).

2-dimethylamino-1,3,4,14b-tetrahydro-2H-pyridino[1,2-d]-dibenzo[b,f](1,4)-oxazepine; melting point HCl salt 260°–265° C (equatorial).

2-dimethylamino-7,11-dimethyl-1,3,4,14b-tetrahydro-2H-pyridino[1,2-d]-dibenzo[b,f](1,4)-oxazepine (oil); Rf in methanol:acetone (9:1) = 0.20 on $SiO_2$ (equatorial).

2-dimethylamino-10-methyl-1,2,3,4,10,14b-hexahydro-pyridino[1,2-d]-dibenzo[b,f](1,4)-diazepine; melting point HCl salt 209°–211° C (equatorial).

2-dimethylamino-10-methyl-13-methoxy-1,2,3,4,10,14b-hexahydro-pyridino[1,2-d]-dibenzo[b,f](1,4)-diazepine; melting point HCl salt: 194°–197° C (equatorial).

2-dimethylamino-10-methyl-13-chloro-1,2,3,4,10,14b-hexahydro-pyridino[1,2-d]-dibenzo[b,f](1,4)-diazepine.

EXAMPLE VI 3-dimethylamino-1,2,3,4,10,14b-hexahydro-dibenzo[c,f]-pyridino[1,2-a]-azepine 3.5 g of 3-keto-1,2,3,4,10,14b-hexahydro-dibenzo[c,f]-pyridino[1,2-a]-azepine are dissolved in 100 ml of ethanol. To this solution are added 4 ml of dimethylamine and 0.4 g of palladium 10% on charcoal. The mixture is hydrogenated while stirring intensively. After the theoretical quantity of hydrogen has been absorbed the catalyst is filtered off and the filtrate evaporated to dryness by means of a film evaporator. Obtained in his manner: 3.6 g of the 3-dimethylamino compound. Treating this compound with a solution of HCl in alcohol results into 2.8 g of the HCl salt, melting point 242°–248° C (equatorial) position).

In the same manner are prepared:

3-dimethylamino-11-methyl-1,3,4,14b-tetrahydro-2H-pyridino[1,2-d]-dibenzo[b,f](1,4)-oxazepine; Rf in methanol:acetone (8:2) = 0.20 (equatorial).

3-dimethylamino-7-trifluoromethyl-1,3,4,14b-tetrahydro-2H-pyridino[1,2-d]-dibenzo[b,f](1,4)-thiazepine; Rf in chloroform:methanol (8:2) = 0.40 on $SiO_2$ (eq.).

3-dimethylamino-8-bromo-1,2,3,4,10,14b-hexahydro-dibenzo[c,f]-pyridino[1,2-a]-azepine; Rf in methanol:acetone (8:2) = 0.20.

3-dimethylamino-10-methyl-1,2,3,4,10,14b-hexahydro-pyridino[1,2-d]-dibenzo[b,f](1,4)-diazepine (oil); Rf = 0.25 in methanol:acetone (8:2) (equatorial).

EXAMPLE VII 2-aminomethyl-1,2,3,4,10,14b-hexahydro-pyridino[1,2-a]-dibenzo[c,f]-azepine To a suspension of 10 g $LiAlH_4$ in 400 ml of dry ether a solution of 8 g of 2-cyano-1,2,3,4,10,14b-hexahydro-pyridino[1,2-a]-dibenzo[c,f]-azepine (axial) in 300 ml of THF is added. Then the mixture is refluxed for 30 minutes, whereupon it is cooled by means of ice. After that 40 ml of water are added to the mixture carefully so as to hydrolyse the excess of $LiAlH_4$. The resulting precipitate is filtered off after which the filtrate is evaporated.

Obtained in this manner: 8.0 g (oil).

Rf in methanol:acetone (9:1) = 0.45 on $SiO_2$.

Melting point maleate salt: 172°–174° C (axial position).

EXAMPLE VIII 3-aminomethyl-11-methyl-1,3,4,14b-tetrahydro-2H-pyridino[1,2-d]-dibenzo[b,f](1,4)-oxazepine 12 g of 3-keto-11-methyl-1,3,4,14b-tetrahydro-2H-pyridino[1,2-d]-dibenzo[b,f](1,4)-oxazepine are hydrogenated with hydrogen and palladium on charcoal in ethanol. After all hydrogen has been absorbed the catalyst is filtered off, whereafter the 3-hydroxy compound is obtained by evaporating the solvent. The product is dissolved in 100 ml of pyridine. While cooling in ice water and stirring 8 g of mesylchloride are added to the solution. The mixture is left to stand at ambient temperature for 18 hours and is poured into water after that.

The aqueous solution is extracted into ether. The ether extracts are washed with 2N sulphuric acid and water and finally dried on dry sodium sulphate.

The dry ethereal solution is evaporated and the residue dissolved in 100 ml of dimethylsulphoxide.

6 g of sodiumcyanide (dry) are added to the solution. While stirring the solution is heated for 3 hours at 100° C, followed by pouring the reaction mixture into water. Extracting with benzene, washing the benzene-extract with water, drying on sodium sulphate and evaporating the solvent yields 8.9 g of the crude nitrile. The product is purified over silicagel by means of chromatography. Reduction of the nitrile with $LiAlH_4$ in ether in the manner as indicated in example VII finally results in 6.2 g of axial 3-aminomethyl compound as an oil.

EXAMPLE IX

The following compounds are prepared from the corresponding cyano-compound by a reduction with LiAlH₄ in the way as indicated in Example VII:

2-aminoethyl-1,2,3,4,10,14b-hexahydro-pyridino[1,2-a]-dibenzo[c,f]-azepine (oil); Rf in methanol:acetone (9:1) = 0.45 (axial), from the corresponding 2-cyanomethyl compound (axial).

2-aminomethyl-13-methyl-1,3,4,14b-tetrahydro-2H-pyridino[1,2-d]-dibenzo[b,f](1,4)-thiazepine (oil); Rf in methanol:acetone (8:2) = 0.35, from the corresponding 2-cyano-compound (axial).

3-aminomethyl-10-methyl-1,2,3,4,10,14b-hexahydro-pyridino[1,2-d]-dibenzo[b,f](1,4)-diazepine, from the corresponding axial 3-cyano-compound.

EXAMPLE X 2-aminoethyl-1,2,3,4,10,14b-hexahydro-pyridino[1,2-a]-dibenzo[c,f]-azepine Diborane gas, obtained from 1.2 g of NaBH₄ and 5.2 ml of BF₃-etherate is let in into a solution of 200 mg of 2-cyanomethylidene-1,2,3,4,10,14b-hexahydro-pyridino[1,2-a]-dibenzo[c,f]-azepine in 15 ml of THF (under nitrogen atmosphere).

After that the mixture is refluxed for 1 hour. The excess of B₂H₅ present is then decomposed by adding ethanol, whereupon the solution is evaporated The residue is dissolved in 18 ml of a mixture of concentrated HCl and water (1:1) whereupon the solution is heated for some time. The acidic water layer is cooled down, made alkaline and then extracted with ether. Evaporating the solvent yields 0.85 g of the title compound as an oil.

EXAMPLE XI 2-amino-1,2,3,4,10,14b-hexahydro-pyridino[1,2-a]-dibenzo[c,f]-azepine 4 g of 2-azido-1,2,3,4,10,14b-hexahydro-pyridino[1,2-a]-dibenzo[c,f]-azepine (axial) is added to a suspension of 3 g of LiAlH₄ in dry ether. The mixture obtained is heated for 1 hour, and after that cooled down. Then 12 ml of water are added to the mixture dropwise, whereby an inorganic precipitate is formed. The inorganic residue is removed by filtration after which the filtrate is evaporated to dryness.

Obtained in this manner: 3.5 g (oil).
Rf in methanol:acetone (9:1) = 0.28 (axial position).
In the same way are prepared:

2-aminio-8-bromo-1,2,3,4,10,14b-hexahydro-pyridino[1,2-a]-dibenzo[c,f]-azepine (oil) from the corresponding 2-azido compound (ax.).

3-amino-1,2,3,4,10,14b-hexahydro-pyridino[1,2-a]-dibenzo[c,f]-azepine from the corresponding 3-azido compound (ax.).

2-aminomethyl-1,2,3,4,10,14b-hexahydro-pyridino[1,2-a]-dibenzo[c,f]-azepine from the corresponding 2-azidomethyl compound (axial); melting point maleate: 170°-174° C (ax.).

2-aminomethyl-1,3,4,14b-tetrahydro-2H-pyridino[1,2-d]-dibenzo[b,f](1,4)-oxazepine, from the corresponding 2-azidomethyl compound (axial).

EXAMPLE XII 2-dimethylaminomethyl-1,2,3,4,10,14b-hexahydro-pyridino[1,2-a]-dibenzo[c,f]-azepine 4 g of the aminomethyl compound obtained in VII are dissolved in 100 ml of methyl-formate. The solution is heated for 24 hours at 40° C. After that the solvent (methylformate) is distilled off in vacuo.

In this manner 4.5 g oily formylamino derivative is obtained. Rf in methanol:acetone (9:1) = 0.90.

4.5 g of this oil dissolved in 250 ml of tetrahydrofurane are added to a suspension of 5 g of lithiumaluminium hydride in 250 ml of dry ether. The suspension is refluxed for 2 hours. After cooling down the suspension with ice, 20 ml of water are added dropwise, after which the mixture obtained is filtered. The filtrate is evaporated to dryness. Obtained in this manner: 4.3 g of axial 2-methylaminomethyl compound.

Rf in methanol:acetone (8:2) = 0.45.

The above-mentioned product is treated with methylformate in the same way once again (melting point N-formyl-N-methyl-amino-methyl compound: 117°-119° C) and reduced after that.

Obtained in this manner: 3.4 g.

Melting point (ax.): 2-dimethylaminomethyl-1,2,3,4,10,14b-hexahydro-pyridino[1,2-a]-dibenzo[c,f]-azepine fumarate: 174°-176° C.

Rf in methanol:acetone (9:1) = 0.40 on SiO₂.

EXAMPLE XIII

Separation of axial and equatorial 2-dimethylamino-1,2,3,4,10,14b-hexahydro-dibenzo[c,f]-pyridino[1,2-a]-azepine 4.38 g of the mother liquor from example IV (mixture of axial and equatorial compound) are dissolved in a mixture of methanol:acetone (9:1). This solution is chromatographed in a column containing 4.5 kg of SiO₂. The column is eluted with a mixture of methanol:acetone (9:1).

Rf axial = 0.38 in methanol:acetone (9:1).
Rf equatorial = 0.16 in methanol:acetone (9:1).
Melting point axial compound as fumarate: 190°-192° C.
Melting point equatorial compound as HCl salt: 266°-269° C.

EXAMPLE XIV 2-dimethylamino-1,2,3,4,10,14b-hexahydro-pyridino[1,2-a]-dibenzo[c,f]-zaepine 4 g of 2-tosyloxy-1,2,3,4,10,14b-hexahydro-pyridino[1,2-a]-dibenzo[c,f]-azepine (eq.) are dissolved in 50 ml of dimethylsulphoxide. After that 15 ml of dimethylamine are added to the solution. This solution is now heated in a sealed ampoule on a vapour-bath for 2 hours. After cooling the solution, it is poured into 300 ml of water after which the mixture is extracted with 3×200 ml of ether. The ether layers are washed and then dried, whereupon the solvent is evaporated and the residue is recrystallized. Yield: 1.3 g.

Melting point 84°-87° C (axial form); melting point fumarate 192°-193° C.

Rf in methanol:acetone (9:1) = 0.45 on SiO₂.

Starting from the corresponding equatorial 2- or 3-tosyloxy-compound the following substance with the 2- or 3-aminoalkyl group in axial position are prepared in the way indicated previously:

2-dimethylamino-8-bromo-1,2,3,4,10,14b-hexahydro-pyridino[1,2-a]-dibenzo[c,f]-azepine (oil); Rf in methanol:acetone (8:2) = 0.40.

2-morpholino-1,2,3,4,10,14b-hexahydro-pyridino[1,2-a]-dibenzo[c,f]-azepine (oil); Rf in methanol:acetone (9:1) = 0.50.

2-pyrrolidino-1,3,4,14b-tetrahydro-2H-pyridino[1,2-d]-dibenzo[b,f](1,4)-oxazepine (oil); Rf in methanol:acetone (9:1) = 0.45.

2-amino-1,2,3,4,10,14b-hexahydro-pyridino[1,2-a]-dibenzo[c,f]-azepine; Rf in methnol:acetone (9:1) = 0.30 on $SiO_2$.

2-methylamino-1,2,3,4,10,14b-hexahydro-pyridino[1,2-a]-dibenzo[c,f]-azepine, oil; Rf in methanol:acetone (9:1) = 0.35 on $SiO_2$.

3-methylamino-1,2,3,4,10,14b-hexahydro-pyridino[1,2-a]-dibenzo[c,f]-azepine (oil); Rf in methanol:acetone (9:1) = 0.30 on $SiO_2$.

3-dimethylamino-7-trifluoromethyl-1,3,4,14b-tetrahydro-2H-pyridino[1,2-d]-dibenzo[b,f](1,4)-thiazepine (oil); Rf in chloroform:methanol (8:2) = 0.45.

2-methylamino-10-methyl-7-methoxy-1,2,3,4,10,14b-hexahydro-pyridino[1,2-d]-dibenzo[b,f](1,4)-diazepine.

Starting from the corresponding equatorial 2- or 3-mesyloxy compounds the following substances are prepared in the way indicated previously (see also example VIII) for the preparation of mesyloxy compounds):

3-dimethylamino-11-methyl-1,2,3,4,14b-tetrahydro-2H-pyridino[1,2-d]-dibenzo[b,f](1,4)-oxazepine (axial).

2-amino-1,2,3,4,10,14b-hexahydro-pyridino[1,2-a]-dibenzo[c,f]-azepine (axial); Rf in methanol:acetone (9:1) = 0.30 on $SiO_2$.

2-dimethylamino-1,2,3,4,10,14b-hexahydro-pyridino[1,2-a]-dibenzo[c,f]-azepine (axial); Rf in methanol:acetone (9:1) = 0.45 $SiO_2$; melting point 84°-86° C.

Starting from the corresponding axial 2-tosyloxymethyl-compound the following compounds are obtained:

2-aminomethyl-1,2,3,4,10,14b-hexahydro-pyridino[1,2-a]-dibenzo[c,f]-azepine; melting point maleate: 170°-175° C (axial).

2-dimethylaminomethyl-1,2,3,4,10,14b-hexahydro-pridino[1,2-a]-dibenzo[c,f]-azepine; melting point 172°-175° C as fumarate (axial).

EXAMPLE XV 2-dimethylamino-methyl-1,2,3,4,10,14b-hexahydro-pyridino[1,2-a]-dibenzo[c,f]-azepine 10 g of (ax.) 2-dimethylaminocarbonyl-1,2,3,4,10,14b-hexahydro-pyrindino[1,2-a]-dibenzo[c,f]-azepine, obtained from the corresponding (ax.) 2-carboxy-1,2,3,4,10,14b-hexahydro-pyridino[1,2-a]-dibenzo[c,f]-azepine (m.p. 207°-209° C) are dissolved in 100 ml tetrahydrofuran (THF). This solution is slowly added to a stirred suspension of 15 g $LiAlH_4$ in THF. The mixture is refluxed for 2 hours and then cooled down.

60 ml of water are now slowly added to the stirred mixture, whereupon the aqueous mixture is filtered to remove the inorganic solids. The filtrate is evaporated in vacuo yielding 9.8 g of the oily residue. The residue is treated with fumaric acid in alcohol yielding the fumaric acid salt of the title compound; melting point 174°-176° C (ax.).

In the same manner the correspondig dimethylaminomethyl derivatives are prepared starting from:

2-carboxy-8-chloro-1,3,4,14b-tetrahydro-2H-pyridino[1,2-d]-dibenzo[b,f](1,4)-oxazepine (ax.); m.p. 211°-214° C.

2-carboxy-7-methyl-1,3,4,14b-tetrahydro-2H-pyridino[1,2-d]-dibenzo[b,f](1,4)-oxazepine (ax.); m.p. 209°-211° C.

2-carboxy-1,2,3,4,10,14b-hexahydro-pyridino[1,2-a]-dibenzo[c,f]-azepine (eq.); m.p. 193°-195° C.

EXAMPLE XVI 2-aminomethyl-1,2,3,4,10,14b-hexahydro-pyridino[1,2-a]-dibenzo[c,f]-azepine 3 g of 2-cyano-1,2,3,4,10,14b-hexahydro-pyrindino[1,2-a]-dibenzo[c,f]-azepine (ax.), is dissolved in 27 ml of concentrated $H_2SO_4$ and 0.3 ml of water. The solution is heated at a steambath for about 2 hours. The reaction mixture is then poured into 500 ml of water, whereupon the aqueous mixture obtained is extracted into ether.

The ether layers are washed with water and dried. The axial-amide residue obtained (m.p. 200°-202° C) is converted into the corresponding axial 2-amino-methyl derivative in the manner as described in Example XV.

Melting point maleate: 172°-174° C.

EXAMPLE XVII 3-dimethylamino-1,2,3,4,10,14b-hexahydro-pyridino[1,2-a]-dibenzo[c,f]-azepine 10.5 g of 2-keto-1,2,3,4,10,14b-hexahydro-pyridino[1,2-a]-dibenzo[c,f]-azepine are dissolved in 1 liter of THF. The solution is cooled down to 0° C. While stirring 30 g of phenyltrimethylammoniumtribromide are added and after 20 min. 250 ml of $NaHCO_3$ solution (saturated).

The mixture is extracted into ether, and the ether layer washed, dried and evaporated. The residue (oil) is purified by means of chromatography. In this way 3 g of crystalline 3-bromide is obtained; melting point 149°-151° C. This substance is dissolved in 90 ml of DMSO (dimethylsulphoxide) to which 10 ml of dimethylamine are added. After the mixture is left to stand for 2 days at room temperature, the excess of dimethylamine and the dimethylsulphoxide is removed by means of a rotary film evaporator. The residue is dissolved in water.

Extraction of this liquid into ether, washing the ether-extract with water, drying it on $Na_2SO_4$ and evaporation of the solvent results in 5.2 g of crude 3-dimethylamino-2-ketone, that is chromatographed over aluminiumoxide.

Obtained in this manner 4.3 g oil. A part of this oil crystallizes after some time: m.p. 118°-122° C. The oil is dissolved in 25 ml glycol, to which 5 g of solid KOH and 6 ml of hydrazinehydrate are added.

The mixture is heated at 150° for 12 hours and then poured into 200 ml of water. The 3-dimethylamino-derivative is isolated by extracting the mixture into an ether-benzene mixture (1:1), washing the extract with water, drying it on $Na_2SO_4$ and evaporating the solvent.

Obtained in this manner: 2.8 g (oil). Melting point as picrate: 161°-164° C.

In the same way are prepared:

3-dimethylamino-11-methyl-1,3,4,14b-tetrahydro-2H-pyridino[1,2-d]-dibenzo[b,f](1,4)-oxazepine; Rf in methanol:acetone (9:1) = 0.15.
3dimethylamino-10-methyl-1,2,3,4,10,14b-hexahydro-pyridino[1,2-d]-dibenzo[b,f](1,4)-diazepine; Rf in methanol:acetone (9:1) = 0.20.
3-morpholino-1,2,3,4,10,14b-hexahydro-pyridino[1,2-a]-dibenzo[c,f]-azepine; Rf in methanol:acetone (8:2) = 0.40.

EXAMPLE XVIII

In the same way as indicated in example XVII a 3keto-2-amino-compound (mixture of 2 axial and 2 equatorial) is converted by means of a Wolff-Kishner reduction into the corresponding 2-amino-compound (mixture of 2axial and 2-equatorial) followed by a separation of both isomers with the aid of a silicagel column as described in example XIII.

In this manner are prepared:

2-dimethylamino-1,2,3,4,10,14b-hexahydro-pyridino[1,2-a]-dibenzo[c,f]-azepine (2-equatorial); melting point HCl salt: 268°-270° C.
2-dimethylamino-1,2,3,4,10,14b-hexahydro-pyridino[1,2-a]-dibenzo[c,f]-azepine (2-axial); melting point: 87°-88° C.
2-dimethylamino-7-trifluoromethyl-1,3,4,14b-tetrahydro-2H-pyridino[1,2-d]-dibenzo[b,f](1,4)-thiazepine (2-equatorial), (oil); Rf = 0.45 in chloroform:methanol (8:2).
2-dimethylamino-11-methyl-1,3,4,14b-tetrahydro-2H-pyridino[1,2-d]-dibenzo[b,f](1,4)-oxazepine (2-equatorial); melting point: 113°-114° C;
2-dimethylamino-10-methyl-1,2,3,4,10,14b-hexahydro-pyridino[1,2-d]-dibenzo[b,f](1,4)-diazepine (2equatorial); melting point: 210°-212° C as HCl salt.
2-dimethylamino-10-methyl-7-methoxy-1,2,3,4,10,14b-hexahydro-pyridino[1,2-d]-dibenzo[b,f](1,4)-diazepine.

EXAMPLE XIX 2-dimethylaminomethyl-1,2,3,4,10,14b-hexahydro-pyridino[1,2-a]-dibenzo[c,f]-azepine A mixture of 4 g of 3-keto-1,2,3,4,10,14b-hexahydro-pyridino[1,2-a]-dibenzo[c,f]-azepine, 60 ml of ethanol, 1.3 g of dimethylamine hydrochloride, 0.5 g of paraformaldehyde and 2 drops of concentrated hydrochloric acid is heated for 6 hours, after which the alcohol is distilled off. The residue is taken up in water and made strongly alkaline with 4N sodium hydroxide. Extraction into ether, washing the extract with water and evaporation of the ether yields 3.7 g of the 2-dimethylaminomethyl-3-keton, that is subjected to a Wolff-Kishner reaction without a further purification. Yield: 2.9 g of the 2-dimethylaminomethyl compound. After purification over a silicagel column the product is treated with an alcoholic fumaric acid solution. The fumarate obtained melts at 168°-173° C.

EXAMPLE XX 3-diethylaminomethyl-1,3,4,14b-tetrahydro-2H-pyridino[1,2-d]-dibenzo[b,f](1,4)-thiazepine A mixture of 8.4 g of the 2-keto-compound, 2.9 g of diethylamine hydrochloride, 1 g of paraformaldehyd and a few drops of concentrated hydrochloric acid in 100 ml ethanol is refluxed for 5 hours. Then the reaction mixture is evaporated as much as possible, whereupon 200 ml of water are added to the residue. The aqueous mixture is made alkaline with 2N NaOH. Extracting into ether and washing, drying and evaporating in the usual way, yields 6.8 g of the 3-diethylaminomethyl-2-keton.

This crude keton is dissolved in a mixture of 40 ml of diethyleneglycol and 10 ml of dimethylsulphoxide. After adding 10 ml of hydrazine hydrate and 4 g of KOH the mixture is stirred for 0.5 hour and then heated at 120° for another hour. Finally the temperature is raised to 160° during 1 hour. After 3 hours' heating at 160° the greater part of the hydrazine hydrate is evaporated in vacuo and the residue poured into water. Extraction into ether and washing, drying and evaporation of the ether extract results in 5.2 g of the 3-diethylaminomethyl compound as a viscous oil. This oil is dissolved in a mixture of methanol:acetone (9:1) and chromatographed over $SiO_2$. After elution with the same solvent the axial compound is obtained as an oil. Rf = 0.35 on $SiO_2$, followed by the equatorial compound: Rf = 0.18 on $SiO_2$.

EXAMPLE XXI

In the same manner as described in Example I are prepared:

2-amino-13-chloro-10-methyl-1,2,3,4,10,14b-hexahydro-pyridino [1,2-d]-dibenzo[b,f](1,4)-diazepine (eq. —$NH_2$);
Melting point di-HCl-salt: 210°-230° (subc.).
2-amino-13-chloro-10-methyl-1,2,3,4,10,14b-hexahydro-pyridino[[1,2-d]-dibenzo[b,f](1,4)-diazepine (ax. —$NH_2$);
Melting point di-HCl-salt: 182°-196° dec. (prepared from the mother liquor of the previous compound.)
2-amino-10-methyl-1,2,3,4,10,14b-hexahydro-pyridino[1,2-d]-dibenzo[b,f](1,4)-diazepine (eq. —$NH_2$);
Melting point maleate: 188°-190° C.

EXAMPLE XXII

In the same manner as described in Example IV are prepared:

2-dimethylamino-7-chloro-10-methyl-1,2,3,4,10,14b-hexahydro-pyridino[1,2-d]-dibenzo[b,f](1,4)-diazepine

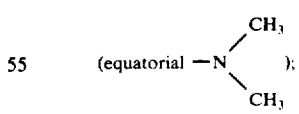

Melting point HCl-salt: 250°-260° C. (subl.)
2-dimethylamino-1,3,4,14b-tetrahydro-2H-pyridino[1,2-d]-dibenzo[b,f](1,4)-thiazepine

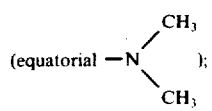

Melting point HCl-salt: 262°-264° C.

EXAMPLE XXIII

In the same manner as described in Example XI are prepared;

2-amino-7-chloro-10-methyl-1,2,3,4,10,14b-hexahydro-pyridino[1,2-d]-dibenzo[b,f](1,4)-diazepine (ax. $NH_2$) from the corresponding 2-azido compound (ax.); Melting point of the maleate salt 219°-220° (dec.).

2-amino-13-chloro-10-methyl-1,2,3,4,10,14b-hexahydro-pyridino[1,2 -d]-dibenzo[b,f](1,4-diazepine (ax. $NH_2$) from the corresponding 2-azido compound (ax.);

Melting point di-HCl-salt 192°-196° (dec.).

EXAMPLE XXIV

In the same manner as described in Example XIV the following compounds are prepared from the corresponding 2-(equatorial)tosyloxy compound:

2-methuylamino-10-methyl-7-chloro-1,2,3,4,10,14b-hexahydro-pyridino[1,2-d]-dibenzo[b,f](1,4)-diazepine (axial $-NHCH_3$); $R_f$ in dichloro-ethane:methanol:water (95:5:o,2) = 0.65 on $Al_2O_3$.

13-chloro-2-dimethylamino-10-methyl-1,2,3,4,10,14b-hexahydro-pyridino[1,2-d]-dibenzo[b,f](1,4)-diazepine (axial $-N(CH_3)_2$);

Melting point of HCl-salt-monohydrate: 145°-150° (dec.).

10-methyl-2-methylamino-1,2,3,4,10,14b-hexahydro-pyridino[1,2-d]-dibenzo[d,f](1,4)-diazepine (axial $-NHCH_3$).

Melting point of maleate salt: 181°-183° C.

EXAMPLE XXV

In the same manner as described in the first part of Example XII are prepared:

13-chloro-10-methyl-2-methylamino-1,2,3,4,10,14b-hexahydro-pyridino[1,2d]-dibenzo[b,f](1,4)-diazepine (eq. $NHCH_3$);

Melting point: di-HCl-salt: 180° C (dec.).

7-chloro-10-methyl-2-methylamino-1,2,3,4,10,14b-hexahydro-pyridino[1,2-d]-dibenzo[b,f](1,4)-diazepine (eq. $NHCH_3$); $R_f$ in dichloro-ethane-methanol:water (95:5:0,2) = 0,5 on $Al_2O_3$.

I claim:

1. A compound of the formula:

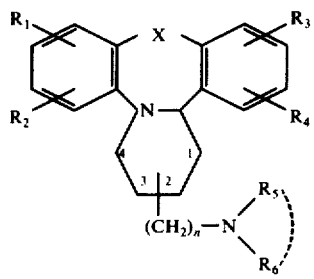

or a pharmaceutically acceptable salt thereof, wherein the group

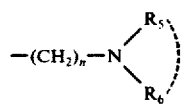

is present at position 2 or 3 in which:

X represents the group $NR_7$, $R_1$, $R_2$, $R_3$ and $R_4$ represent hydrogen, hudroxy, halogen, alkyl containing 1 to 6 carbon atoms, alkoxy containing 1 to 6 carbon atoms, alkylthio containing 1 to 6 carbon atoms or trifluoromethyl, $R_5$, $R_6$ represent hydrogen, alkyl containing 1 to 6 carbon atoms, phenylalkyl in which the alkyl group contains 1 to 4 carbon atoms, or $R_5$ together with $R_6$ and the nitrogen atom represent a hererocyclic 5 or 6 membered ring selected from the group consisting pyrrolino, pyrrolidino, piperidino, oxazolidino, morpholino, and piperazino, $R_7$ represents hydrogen or alkyl containing 1 to 4 carbon atoms, and n is the number 0, 1, 2 or 3.

2. A compound of the formula according to claim 1, in which the (alkyl)amino moiety is present at position 2.

3. A compound of the formula according to claim 1, in which n is the number 0 or 1.

4. A compound of the formula according to claim 1, in which $R_7$ represents alkyl.

5. A compound of the formula:

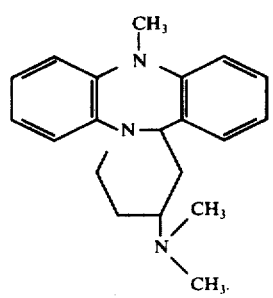

* * * * *